US00PP35789P2

(12) United States Plant Patent
Clark

(10) Patent No.: US PP35,789 P2
(45) Date of Patent: Apr. 30, 2024

(54) ***COLEUS* PLANT NAMED 'UF22-284-1'**

(50) Latin Name: *Coleus scutellarioides.*
Varietal Denomination: UF22-284-1

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,292

(22) Filed: Jun. 20, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373
CPC ..... A01H 5/12; A01H 5/00; A01H 6/50
See application file for complete search history.

(56) References Cited

U.S. PATENT DOCUMENTS

PP27,126 P3 * 8/2016 Clark ..... A01H 6/50
Plt./469

OTHER PUBLICATIONS

Campbell's Nursery Coleus, Stained Glassworks Copper retrieved on Oct. 23, 2023 at https://www.campbellsnursery.com/product/landscapeplants/annuals/springandsummerannuals/coleus-stained-glassworks-copper/, 3 pp. (Year: 2023).*

* cited by examiner

*Primary Examiner* — June Hwu
(74) *Attorney, Agent, or Firm* — Koenig IP Works, PLLC; Katherine Koenig

(57) ABSTRACT

'UF22-284-1' is a new *Coleus* plant, selected for having a combination of desirable traits that make it well-suited for use as an annual plant in the summer landscape. 'UF22-284-1' was selected for its consistent foliage color patterning and for its fast growth rate and vigor in the greenhouse and landscape. 'UF22-284-1' has foliage that is predominantly colored yellow green with dark greyish red coloration broadly concentrated in the center of the leaf blade and narrowing toward the leaf apex along the leaf veins in a netted pattern on the upper surface of mature leaves. 'UF22-284-1' maintains these contrasting colors and patterns in both sun and shade until the end of the garden season. 'UF22-284-1' is upright in habit and is highly branched with spreading in form, growing wider than it does tall.

3 Drawing Sheets

Genus and species: *Coleus scutellarioides.*
Cultivar denomination: 'UF22-284-1'.

BACKGROUND OF THE NEW CULTIVAR

The invention relates to a new and distinct cultivar of *Coleus* plant named 'UF22-284-1'. The new cultivar 'UF22-284-1' originated from an open pollination conducted in May-November 2021 in Citra, Florida, between the female *Coleus* plant 'UF20-14-3' (unpatented) and an unknown male *Coleus* plant. A single seedling was chosen in May 2022 for further asexual propagation in Gainesville, Florida.

The new cultivar 'UF22-284-1' has been reproduced asexually for over 11 months through vegetative meristem tip cuttings and has been found to retain its distinctive characteristics through successive asexual propagations. 'UF22-284-1' was first propagated asexually by vegetative meristem tip cuttings in May 2022 in Gainesville, Florida, and has remained true-to-type since that time.

Plant Breeder's Rights for the new cultivar 'UF22-284-1' have not been applied for, and 'UF22-284-1' has not been made publicly available more than one year prior to the filing date of this application.

SUMMARY OF THE INVENTION

The new cultivar 'UF22-284-1' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF22-284-1' was selected for its consistent foliage color patterning, and also for its fast growth rate and vigor in the greenhouse and landscape. 'UF22-284-1' has foliage that is predominantly yellow green with greyish red colored veins in a netted pattern. Normally this color combination changes in either full sun (predominantly dark brick red) or full shade (predominantly dark green), with the consistent loss of the distinctive patterning. However, 'UF22-284-1' maintains consistent yellow green color with distinct greyish red veins in both sun and shade.

The following are the most outstanding and distinguishing characteristics of 'UF22-284-1' when grown under normal horticultural practices in Gainesville, Florida: (1) 'UF22-284-1' has the combination of vigorous, upright habit and spreading growth form, excellent heat tolerance, and consistent yellow green leaves with greyish red veins in a netted pattern that are significantly different than other *Coleus* plants; (2) it has superior stability in foliage color in both sun and shade conditions, and it has a vigorous growth habit with excellent lateral branching, making it suitable for propagators and producers; and (3) 'UF22-284-1' has been observed to have long-season performance in landscape trials in Gainesville, Florida.

When 'UF22-284-1' is compared to the female parent 'UF20-14-3', both have ovate-shaped leaves that are similar in size with crenate margins. However, 'UF22-284-1' has leaves that are predominantly colored yellow green with dark greyish red coloration broadly concentrated in the center of the leaf blade and narrowing toward the leaf apex along the leaf veins in a netted pattern on the upper surface of mature leaves, whereas 'UF20-14-3' has leaves that are predominantly colored dark crimson red with chartreuse margins. Both 'UF22-284-1' and 'UF20-14-3' have similar overall upright plant habit and spreading form.

DESCRIPTION OF THE FIGURES

This new *Coleus* cultivar 'UF22-284-1' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
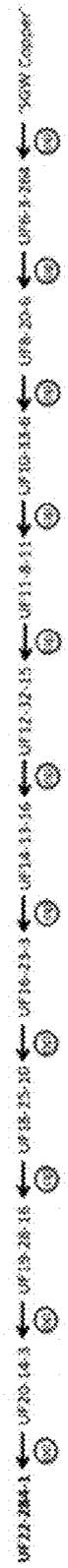
FIG. 1 shows the pedigree of the new *Coleus* cultivar 'UF22-284-1' as is shown and described herein. 'SGW Copper' is also known commercially as Stained Glass-works® Copper (Dümmen Group B.V. (besloten vennootschap (b.v.); NETHERLANDS))
Figure 2:
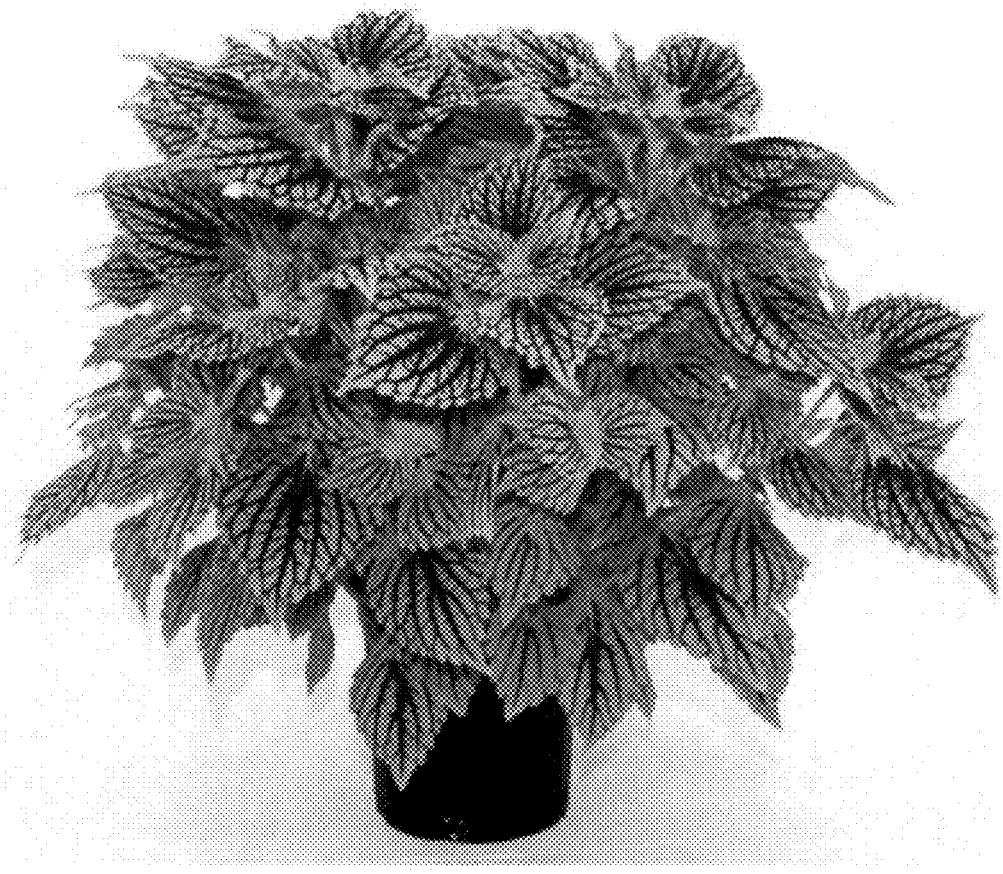
FIGS. 2 and 3 were taken from plants grown eleven weeks from unrooted cuttings in September-December 2022 in a glass-covered greenhouse in Gainesville, Florida.
Figure 3:
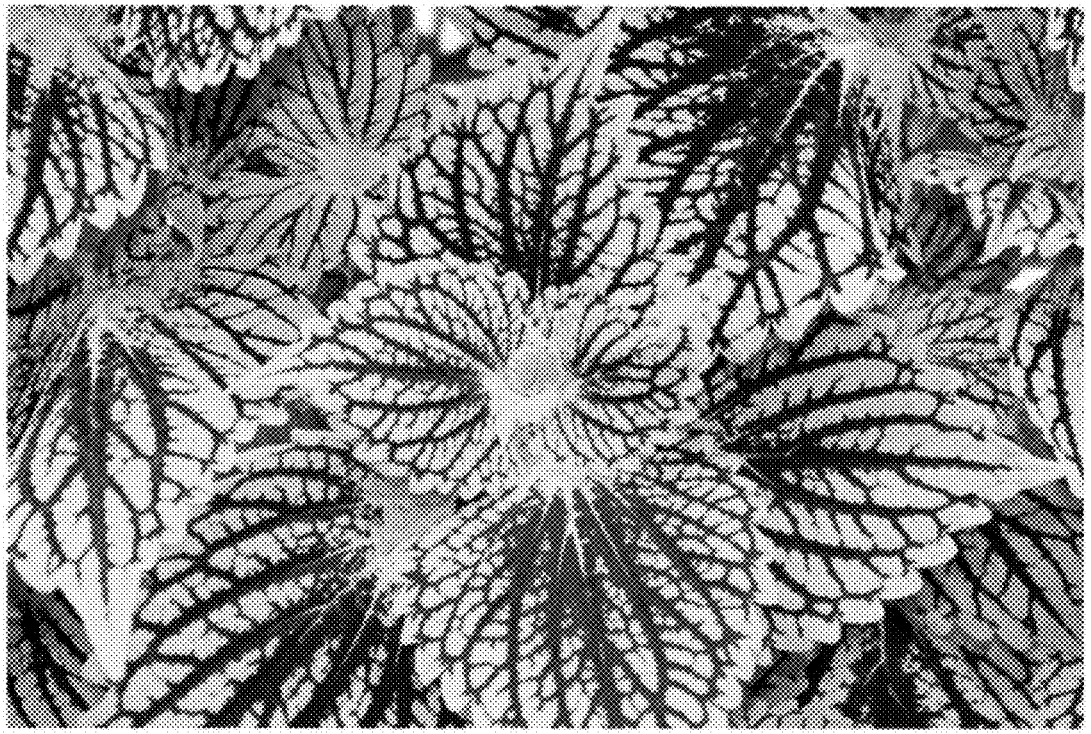

Foliage color was determined under full sun conditions in the middle of the day in a glass-covered greenhouse. Color references are to The RHS Colour Chart of The Royal Horticultural Society of London (RHS), 2007 5th Edition. *Coleus* leaves are rarely one solid color but encompass hues, shades and tints, and color patterns differ from one genotype to another due to varying levels of variegation. The following detailed description of 'UF22-284-1' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

Botanical Description

Botanical classification:

*Family.*—Lamiaceae.

*Botanical name.*—*Coleus scutellarioides.*

*Common name.*—*Coleus.*

*Cultivar name.*—'UF22-284-1'.

Parentage:

*Female or seed parent.*—'UF20-14-3'.

*Male or pollen parent.*—Unknown.

Plant description:

*Form.*—Spreading.

*Habit.*—Upright.

*Height* (*from top of soil*).—35-40 cm.

*Width* (*horizontal plant diameter*).—60-65 cm.

Propagation:

*Type cuttings.*—Vegetative meristems having at least 1 node.

*Time to initiate roots.*—3-4 days.

*Time to produce a rooted cutting.*—7-10 days.

*Root habit.*—Fibrous.

*Root description.*—Callus forms in 2-3 days, roots initiate in 3-4 days and become a highly branched cutting in 7-10 days.

Branches:

*Quantity per plant.*—8-9.

*Branch color.*—RHS 143B (yellow green).

*Texture.*—Smooth.

*Pubescence.*—Not present.

*Stem description.*—Square-shaped stem.

*Branch diameter.*—0.8-0.9 cm at the base of a 35-cm-long branch.

*Branch length.*—35-40 cm.

*Internode length.*—3-4 cm measured at mid-branch.

*Anthocyanin.*—Not present.

Leaves:

*Quantity of leaves per branch.*—18-20.

*Arrangement.*—Opposite.

*Fragrance.*—Not fragrant.

*Shape.*—Ovate.

*Length.*—13-14 cm.

*Width.*—10-11 cm.

*Apex.*—Broadly acute.

*Base.*—Attenuate.

*Margin.*—Lobed.

*Margin depth.*—Medium.

*Leaf texture.*—Adaxial (top): Pulverulent. Abaxial (bottom): Smooth.

*Venation color.*—Upper surface: RHS 142C (light yellow green) at the base and toward the center, turning RHS N186C (greyish red) from the center toward the leaf margins. Lower surface: RHS 142C (light yellow green).

*Venation pattern* (*both upper and lower surfaces*).—Reticulate.

*Color, immature leaf.*—Upper surface: Emerging leaves are mostly RHS 144A (yellow green), and newly expanded leaves are RHS 144A (yellow green) with RHS N186C (greyish red) concentrated around the leaf veins. Immature leaves located in the interior of the plant (that are more shaded) are mostly RHS 144A (yellow green) with less RHS N186C (greyish red) venation than immature leaves located near the exterior of the plant (that receive more light). Lower surface: RHS 143A (yellow green).

*Color, mature leaf.*—Upper surface: RHS 144A (yellow green) with RHS N186C (greyish red) broadly concentrated in the center of the leaf blade and narrowing toward the leaf apex along the leaf veins in a netted pattern. Lower surface: RHS 143A (yellow green).

*Petiole length.*—Approximately 5 cm.

*Petiole diameter.*—0.3-0.4 cm.

*Petiole color.*—RHS 140B (yellowish green).

*Petiole texture.*—Smooth, no pubescence.

Flowers and seeds: Flowers and seeds have not been observed during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with Known Cultivars: When compared to the *Coleus* cultivar 'UF10-45-12' (U.S. Plant Pat. No. 27,126, commercial name Coleosaurus), the new *Coleus* cultivar 'UF22-284-1' has a leaf coloration of yellow green with dark greyish red coloration broadly concentrated in the center of the leaf blade and narrowing toward the leaf apex along the leaf veins on the upper surface of mature leaves, whereas 'UF10-45-12' has a similar leaf coloration of yellow green but has a dark red coloration more uniformly distributed across the leaf blade on the upper surface of mature leaves.

What is claimed is:

1. A new and distinct *Coleus scutellarioides* plant named 'UF22-284-1' as shown and described herein.

* * * * *